United States Patent
Heinrich et al.

(10) Patent No.: US 7,253,202 B2
(45) Date of Patent: Aug. 7, 2007

(54) SUBSTITUTED BENZODIOXEPINES

(75) Inventors: Timo Heinrich, Gross-Umstadt (DE); Henning Böttcher, Darmstadt (DE); Kai Schiemann, Darmstadt (DE); Günter Hölzemann, Seeheim-Jugenheim (DE); Christoph van Amsterdam, Darmstadt (DE); Gerd Bartoszyk, Weiterstadt (DE); Hartmut Greiner, Weiterstadt (DE); Christoph Seyfried, Seeheim-Jugenheim (DE); Michel Brunet, Toussieu (FR); Jean Zeiller, Lyons (FR); Jean Berthelon, Lyons (FR)

(73) Assignee: Merck Patent GmbH, Darmstadt (DE)

( * ) Notice: Subject to any disclaimer, the term of this patent is extended or adjusted under 35 U.S.C. 154(b) by 230 days.

(21) Appl. No.: 10/539,515

(22) PCT Filed: Nov. 27, 2003

(86) PCT No.: PCT/EP03/13373

§ 371 (c)(1),
(2), (4) Date: Jun. 17, 2005

(87) PCT Pub. No.: WO2004/058746

PCT Pub. Date: Jul. 15, 2004

(65) Prior Publication Data
US 2006/0167078 A1   Jul. 27, 2006

(30) Foreign Application Priority Data
Dec. 20, 2002 (EP) .................................. 02028596

(51) Int. Cl.
C07D 405/12 (2006.01)
A61K 31/357 (2006.01)
A61K 31/404 (2006.01)

(52) U.S. Cl. ........................ 514/414; 514/415; 548/454
(58) Field of Classification Search ................ 548/454; 514/414, 415
See application file for complete search history.

(56) References Cited

U.S. PATENT DOCUMENTS 3,944,560 A * 3/1976 Wasson et al. .............. 548/135

FOREIGN PATENT DOCUMENTS

| EP | 0 769 496 | 4/1997 |
|---|---|---|
| GB | 2 007 656 | 5/1979 |
| WO | WO 03 87086 | 10/2003 |

* cited by examiner

*Primary Examiner*—Joseph K. McKane
*Assistant Examiner*—Michael P. Barker
(74) *Attorney, Agent, or Firm*—Millen, White, Zelano & Branigan, P.C.

(57) ABSTRACT

Benzodioxepines of the formula (I) and physiologically tolerated salts and solvates thereof, in which $R^1$, $R^2$, $R^3$, $R^4$, A, B, a and b have the meanings indicated in claim 1, are ligands of the 5HT1A receptors and/or the 5HT4 receptors with simultaneously strong serotonin reuptake inhibition. They can be employed for the treatment and prophylaxis of various diseases

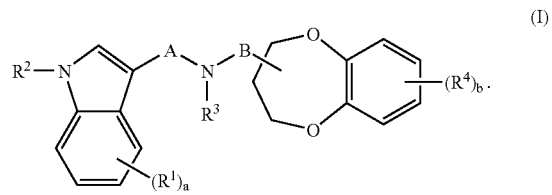

20 Claims, No Drawings

SUBSTITUTED BENZODIOXEPINES

The invention relates to substituted benzodioxepines of the formula I

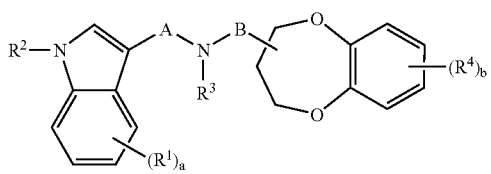

in which
R$^1$, independently of one another, is selected from alkyl, (CH$_2$)$_m$OD, (CH$_2$)$_m$CN, (CH$_2$)$_m$COR$^5$ or (CH$_2$)$_m$CH$_2$R5, where m=0 or 1
R$^2$, R$^3$, independently of one another, is selected from H, alkyl having 1 to 5 C atoms,
R$^4$, independently of one another, is selected from alkyl having 1 to 5 C atoms, heteroalkyl having 1 to 5 C atoms, alkoxy having 1 to 5 C atoms, alkoxyalkyl having 2 to 5 C atoms, Hal, CN, COR$^5$ or OH,
R$^5$ stands for OD, NH$_2$, NHD or ND$_2$,
A stands for C$_n$H$_{2n}$ where n=2, 3, or 4,
B stands for C$_p$H$_{2p}$ where p=0, 1, 2, 3 or 4,
D, independently of one another, is selected from H, alkyl having 1 to 5 C atoms, alkoxyalkyl having 2 to 5 C atoms, aryl or aralkyl,
a, b stand for 0, 1 or 2 and
Hal stands for F, Cl, Br or I, and physiologically tolerated salts and solvates thereof.

Substituted benzodioxepines and the use thereof as pharmaceutical active ingredients for the treatment of hypertension are described, for example, in DE 2847623, BE 613210, BE 613212 and BE 613215.

The invention was based on the object of finding novel compounds having valuable properties, in particular those which are suitable for the preparation of medicaments.

It has now been found that the compounds of the formula I and physiologically tolerated salts and solvates thereof have particularly valuable pharmacological properties. In particular, they exhibit particular effects on the central nervous system, especially 5HT reuptake-inhibiting and 5HT-1A-agonistic actions and in some cases very high affinity to the 5HT4 receptor subtype. The compounds according to the invention furthermore exhibit serotonin-agonistic or antagonistic properties.

Compounds of the formula I have particularly valuable pharmacological properties. The compounds are particularly suitable for the preparation of medicaments for anxiolytics, antidepressants, antipsychotics, neuroleptics and hypertonics. The compounds of the formula I are suitable for the treatment and/or prophylaxis of various diseases of the central nervous system, such as, for example, strokes, cerebral ischaemia and for reducing secondary damage caused by ischaemia, trauma, hypoglycaemia, schizophrenia, depression, dementia, dyskinesia, neurodegenerative diseases, such as Parkinson's disease, ALS, Alzheimer's disease, Lewy bodies dementia or Huntington's syndrome, Tourette's syndrome, anxiety, learning and memory impairment and sleeping disorders, inflammation-induced hyperalgesia, cerebral oedemas, under-supply states (hypoxia).

The compounds of the formula I can furthermore be employed for the treatment and/or prophylaxis of inflammatory intestinal diseases and the associated disease symptoms, of functional gastrointestinal diseases which are associated with pain and/or increased or reduced peristalsis, in particular irritable bowel syndrome (IBS), or for the treatment of non-ulcer-related dyspepsia, obstipation, in particular opiode-induced obstipation, of arthritis, migraine, psoriasis or other irritative skin diseases, dysmenorrhoea and fibromylagia.

The compounds of the formula I are also suitable for the treatment and/or prophylaxis of pain states, in particular pain oversensitivity reactions occurring in back complaints, burn injuries, sunburn and rheumatic diseases, and for the treatment of postoperative pain and the ileus which frequently occurs after abdominal operations. In addition, the compounds of the formula I preferably have an analgesic, antiinflammatory, antiasthmatic, diuretic, anticonvulsive, neuroprotective and/or antitussuive action and are therefore preferably suitable for the treatment of inflammation-induced hyperalgesia, for the treatment of cerebral oedema, in conditions of under-supply (hypoxia), conditions of pain, and for the amelioration of secondary damage of ischaemia The compounds of the formula I find further applications in the treatment and/or prophylaxis of diseases of the bladder, in particular of irritable bladder, cytalgia, cystaigia, neuralgia or bladder neurosis. The term irritable bladder stands for a chronic condition of irritation of the lower urinary tract which occurs, in particular, in women. Symptoms are dysuria, imperative desire to urinate, pollakiuria, suprapubic and diffuse pain on sitting. There is frequently a pronounced discrepancy between subjective complaints and the objective findings. The most frequent causes are disorders of the psychovegetative or endocrine system. Irritable bladder should be differentiated from other clinical pictures, such as urinary tract infections and changes in the lower urinary tract, diseases of adjacent pelvic organs or CNS or spinal cord diseases (for example multiple sclerosis).

For ex-vivo detection of serotonin reuptake inhibition, use can be made, for example, of synaptosomal uptake inhibition (Wong et al., Neuropsychopharmacol. 8 (1993), 23-33) and p-chloroamphetamine antagonism (Fuller et al., J. Pharmacol. Exp. Ther. 212 (1980), 115-119).

Binding properties of the compounds of the formula I can be determined, for example, by the 5-HT1A (serotonin) binding test (Matzen et al., J. Med. Chem., 43 (2000), 1149-1157, in particular page 1156 with reference to Eur. J. Pharmacol.: 140 (1987), 143-155).

For determination of the binding properties of the compounds of the formula I to the 5-HT4 receptor, use can be made of the test according to Grossman et al. (Grossman et al., Br. J. Pharmacol. 109, (1993), 618-24).

The invention relates to the compounds of the formula I and and/or enantiomers, diastereomers, racemates thereof and physiologically tolerated salts and solvates thereof as ligands of the 5 HT1A receptors and/or the 5HT4 receptors with simultaneously strong serotonin reuptake inhibition.

The invention accordingly relates to the compounds of the formula I and/or enantiomers, diastereomers, racemates thereof and physiologically tolerated salts and solvates thereof as ligands of the 5HT1A receptors and/or the 5HT4 receptors with simultaneously strong serotonin reuptake inhibition for the treatment and/or prophylaxis of various diseases, such as, for example, strokes, cerebral ischaemia and for reducing secondary damage caused by ischaemia, trauma, hypoglycaemia, schizophrenia, depression, dementia, dyskinesia, neurodegenerative diseases, such as Parkinson's disease, ALS, Alzheimer's disease, Lewy bodies dementia or Huntington's syndrome, Tourette's syndrome, anxiety, learning and memory impairment, sleeping disorders, inflammation-induced hyperalgesia, cerebral oedemas, under-supply states (hypoxia), inflammatory intestinal diseases and the associated disease symptoms, functional gastrointestinal diseases which are associated with pain and/or increased or reduced peristalsis, in particular irritable bowel syndrome, for the treatment and/or prophylaxis of non-ulcer-related dyspepsia, obstipation, in particular opiode-induced obstipation, arthritis, migraine, psoriasis or other irritative skin diseases, dysmenorrhoea, fibromylagia, pain states, in particular pain oversensitivity reactions occurring in back complaints, burn injuries, sunburn and rheumatic diseases, postoperative pain and the ileus which frequently occurs after abdominal operations, diseases of the bladder, in particular of irritable bladder, cytalgia, cystalgia, neuralgia or bladder neurosis.

The invention accordingly also relates to the use of the compounds of the formula I and/or enantiomers, diastereomers, racemates thereof and physiologically tolerated salts and solvates thereof for the preparation of a medicament for the treatment and/or prophylaxis of various diseases, such as, for example, strokes, cerebral ischaemia and for reducing secondary damage caused by ischaemia, trauma, hypoglycaemia, schizophrenia, depression, dementia, dyskinesia, neurodegenerative diseases, such as Parkinson's disease, ALS, Alzheimer's disease, Lewy bodies dementia or Huntington's syndrome, Tourette's syndrome, anxiety, learning and memory impairment, sleeping disorders, inflammation-induced hyperalgesia, cerebral oedemas, under-supply states (hypoxia), inflammatory intestinal diseases and the associated disease symptoms, functional gastrointestinal diseases which are associated with pain and/or increased or reduced peristalsis, in particular irritable bowel syndrome, for the treatment and/or prophylaxis of non-ulcer-related dyspepsia, obstipation, in particular opiode-induced obstipation, arthritis, migraine, psoriasis or other irritative skin diseases, dysmenorrhoea, fibromylagia, pain states, in particular pain oversensitivity reactions occurring in back complaints, burn injuries, sunburn and rheumatic diseases, postoperative pain and the ileus which frequently occurs after abdominal operations, diseases of the bladder, in particular of irritable bladder, cytalgia, cystalgia, neuralgia or bladder neurosis.

The compounds of the formula I and/or enantiomers, diastereomers, racemates thereof and physiologically tolerated salts and solvates thereof can be employed as medicament active ingredient in human and veterinary medicine.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The compounds of the formula I can preferably be obtained by reacting compounds of the formula II with compounds of the formula III, preferably with compounds of the formula IIIa or compounds of the formula IV with compounds of the formula V.

The invention therefore relates to a process for the preparation of the compounds of the formula I and physiologically tolerated salts and solvates thereof, characterised in that a) a compound of the formula II

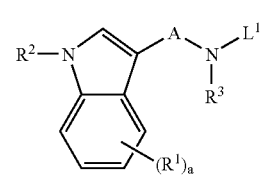

in which $L^1$ denotes H or a metal ion and $R^1$, $R^2$, $R^3$, A and a have the meanings indicated above and below for the compounds of the formula I, b) is reacted with a compound of the formula III

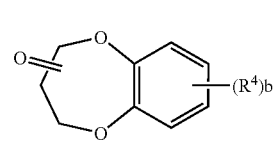

preferably with a compound of the formula IIIa

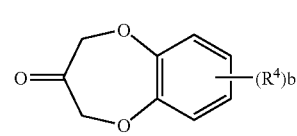

where, in the formula III and IIIa, $R^4$ and b have the meanings indicated above and below for the compounds of the formula I, c) a reduction step is optionally carried out and d) the resultant compound of the formula I is optionally converted into one of its salts by treatment with an acid.

The invention furthermore relates to a process for the preparation of the compounds of the formula I and physiologically tolerated salts and solvates thereof, characterised in that a) a compound of the formula IV

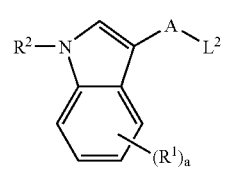

in which $L^2$ denotes Cl, Br, I, OH, a reactively esterified OH group or a diazonium group and $R^1$, $R^2$, A and a have the meanings indicated above and below for the compounds of the formula I, b) is reacted with a compound of the formula V

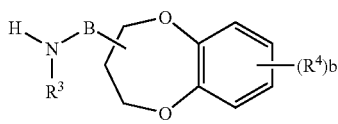

in which $R^3$, $R^4$, B and b have the meanings indicated above and below for the compounds of the formula I, and optionally c) the resultant compound of the formula I is converted into one of its salts by treatment with an acid.

The processes according to the invention can be carried out in the sense of a one-pot reaction, i.e. isolation and/or purification steps are omitted as far as possible and only the desired end product is purified and/or isolated. Alternatively, a purification and/or isolation step can be carried out after each of the said reaction steps. Mixed forms of the above-described procedures are also conceivable.

Suitable purification and isolation steps are known to the person skilled in the art, for example from Houben-Weyl, Methoden der organischen Chemie [Methods of Organic Chemistry], Georg-Thieme-Verlag, Stuttgart.

The starting materials, for example the compounds of the formula II, III, IIIa, IV or V, may, if desired, also be formed in situ so that they are not isolated from the reaction mixture, but instead immediately converted further into the compound of the formula I.

The reaction both of the compounds of the formula II with the compounds of the formula III, preferably with the compounds of the formula IIIa, and also the reaction of the compounds of the formula IV with the compounds of the formula V, is generally carried out in an inert solvent.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, water, or mixtures of the said solvents.

The reaction of the compounds of the formula IV with compounds of the formula V is generally carried out in the presence of an acid-binding agent. Suitable acid-binding agents are all bases which are usual in organic synthetic chemistry, both inorganic and organic, preferably organic bases. Examples of suitable organic bases are triethylamine, diisopropylamine (DIPEA), dimethylaniline, pyridine or quinoline. The addition of an inorganic base, such as, for example, an alkali or alkaline earth metal hydroxide, carbonate or bicarbonate, or of another salt of a weak acid of the alkali or alkaline earth metals, preferably of potassium, sodium, calcium or caesium, may also be favourable.

The reaction of the compounds of the formula II with the compounds of the formula III or IIIa is generally likewise carried out in one of the above-mentioned inert solvents. It may likewise be advantageous to carry out a reduction step after the reaction of the compound of the formula II and III or IIIa. Suitable reduction steps are known to the person skilled in the art. The reduction step can preferably be carried out by reduction using metal hydrides, for example complex metal hydrides. Examples of metal hydrides employed are sodium hydride, calcium hydride, sodium borohydride and lithium aluminium hydride, diisobutylaluminium hydride or $NaAl(OCH_2CH_2OCH_3)_2H_2$, as well as diborane, if desired with addition of catalysts, such as $BF_3$, $AlCl_3$ or LiBr. Preference is given to reduction using complex metal hydrides, such as $NaBH_4$ and $LiAlH_4$. Particular preference is given to reduction using $NaBH_4$. Suitable solvents for this purpose are, in particular, ethers, such as diethyl ether, di-n-butyl ether, THF, dioxane, diglyme or 1,2-dimethoxyethane, as well as hydrocarbons, such as benzene. For a reduction using $NaBH_4$, primarily alcohols, such as methanol or ethanol, furthermore water and aqueous alcohols are suitable as solvent.

Depending on the conditions used, the reaction time is between a few minutes and 14 days, the reaction temperature is between about $-30°$ C. and $180°$ C., normally between $-20°$ C. and $140°$ C., preferably between $-10°$ C. and $130°$ C. and in particular between about $0°$ C. and about $120°$ C.

A base of the formula I can be converted into the associated acid-addition salt using an acid, for example by reaction of equivalent amounts of the base and the acid in an inert solvent, such as ethanol, and subsequent evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethane-sulfonic acid, benzenesulfonic acid, p-toluenesulfonic acid, naphthalene-mono- and disulfonic acids, laurylsulfuric acid. Salts with physiologically untolerated acids, for example picrates, can be used for the isolation and/or purification of the compounds of the formula I.

The invention relates, in particular, to the compounds of the formula I in which at least one of the said radicals has one of the preferred meanings indicated above or below.

For the purposes of the present invention, alkyl denotes a linear or branched alkyl radical, preferably an unbranched alkyl radical which has 1, 2, 3, 4 or 5 C atoms, preferably 1, 2, or 3 C atoms, and may be mono- or poly by halogen (Hal), for example perfluorinated. If an alkyl radical is substituted by halogen, it preferably has, independently of the number of carbon atoms of the alkyl radical, 1, 2, 3, 4 or 5 halogen atoms. Thus, for example, a methyl group (alkyl radical having 1 carbon atom) may be mono-, di- or trisubstituted by halogen, and an ethyl group (alkyl radical having 2 carbon atoms) may be mono-, di-, tri-, tetra- or pentasubstituted by halogen.

For alkyl groups having more than 2 carbon atoms, the same preferably applies as for ethyl groups. Alkyl particularly preferably stands for methyl, ethyl, trifluoromethyl, pentafluoroethyl or propyl, furthermore preferably for isopropyl, butyl, isobutyl, sec-butyl or tert-butyl, but also for n-pentyl, neopentyl or isopentyl.

The term alkoxy encompasses the radicals —O-alkyl, where alkyl has the above-mentioned meaning. Preference is given to the radicals methoxy, ethoxy and propoxy.

The term "alkoxyalkyl" preferably encompasses straight-chain radicals of the formula $C_UH_{2U+1}$—O—$(CH_2)_v$-, in which u and v each, independently of one another, denote 1, 2, 3 or 4, where the sum of u and v does not, however, exceed 5. Particularly preferably, u=1 and v=1, 2, 3 or 4.

The term "aryl" preferably encompasses an unsubstituted or mono- or polysubstituted benzene ring, for example an unsubstituted or substituted phenyl radical or an unsubstituted or mono- or polysubstituted system of benzene rings, such as, for example, anthracene, phenanthrene or naphthalene ring systems. Examples of suitable substituents include alkyl, alkoxy, oxo, hydroxyl, mercapto, amino, nitro, cyano and halogen radicals.

The term "aralkyl" preferably encompasses an aryl radical as defined above, connected to an alkyl radical as defined above. Examples of suitable aralkyl radicals include, but are not restricted to, benzyl, phenylpropyl, phenylbutyl and the like.

The term "heteroalkyl" preferably encompasses an alkyl radical as defined above in which one or more carbon atoms have been replaced by at least one oxygen, nitrogen or sulfur atom, for example an alkyloxy group, such as, for example, kethoxy or ethoxy, or a methoxymethyl, cyano or 2,3-dioxyethyl group, polyoxyethylene or -propylene radicals or polythioethylene or propylene radicals.

In the compounds of the formula II, $L^1$ preferably denotes H or a group which activates the amino function, for example a metal ion. In a particularly preferred embodiment, $L^1$ denotes H. Suitable metal ions are, in particular, alkali metal, alkaline earth metal or aluminium ions. Preferred metal ions are alkali metal ions, in particular Li, Na or K. In the case of polyvalent metal ions, a complex of metal ion and two or more compounds of the formula III often forms, where the complex stoichiometrically generally includes as many compounds of the formula III as corresponds to the valency of the metal ion.

In the compounds of the formula IV, $L^2$ preferably denotes Cl, Br, I, OH, a reactively modified OH group, in particular a reactively esterified OH group, such as an alkylsulfonyloxy group having 1-6 C atoms (preferably methylsulfonyloxy) or arylsulfonyloxy group having 6-10 C atoms (preferably phenyl- or p-tolylsulfonyloxy), or a diazonium group. In a particularly preferred embodiment, $L^2$ denotes Cl.

For the purposes of the present invention, the term solvates encompasses a complex of variable stoichiometry comprising a dissolved compound of the formula 1 or a salt thereof and a solvent which is inert with respect to the biological activity of the compound of the formula I. Examples of suitable solvents include, for example, water, methanol, ethanol or acetic acid.

The present invention preferably relates to compounds of the formula I in which the radicals $R^2$ and $R^3$ stand for H, where $R^1$, $R^4$, $R^5$, A, B, D, a, b and Hal have the meanings indicated above and below for the compounds of the formula I.

Preference is furthermore given to compounds of the formula I in which the radicals $R^2$ and $R^3$ stand for H and at least one radical $R^1$ stands for $(CH_2)_mCN$, where $R^4$, $R^5$, A, B, D, a, b, m and Hal have the meanings indicated above and below for the compounds of the formula I. Of these compounds, particular preference is given to those compounds in which $R^1$ is in the 5-position of the indole ring and a preferably stands for 1 and m preferably stands for 0.

Further preferred compounds of the formula I are those in which A stands for $C_nH_{2n}$ where n=4 and B stands for $C_pH_{2p}$ where p=1 or 0, where $R^1$, $R^2$ $R^3$, $R^4$, $R^5$, D, a, b, m and Hal have the meanings indicated above and below for the compounds of the formula I.

Particularly preferred compounds of the formula I are those in which $R^1$ stands for $(CH_2)_mCN$ in the 5-position of the indole ring and a stands for 1 and m stands for 0, $R^2$ and $R^3$ stand for H, A stands for $C_nH_{2n}$ where n=4 and B stands for $C_pH_{2p}$ where p=1 or 0, where, $R^4$, $R^5$, D, and Hal have the meanings indicated above and below for the compounds of the formula I.

The radicals mentioned above as preferred are also preferred in the compounds of the formulae II, III, IIIa, IV and V.

In a very particularly preferred embodiment of the present invention, the compounds of the formula I are selected from the following sub-formulae Ia to Ie and physiologically tolerated salts and solvates thereof.

Ia

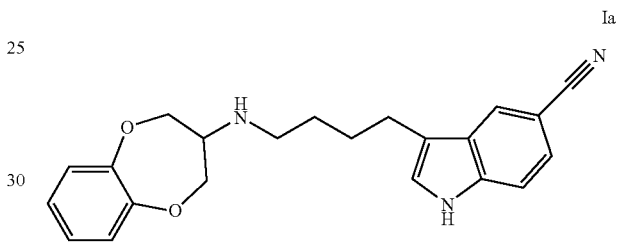

N-(3,4-Dihydro-2H-1,5-benzodioxepin-3-yl)-4-(5-cyano-3-indolyl)butyl-amine

Ib

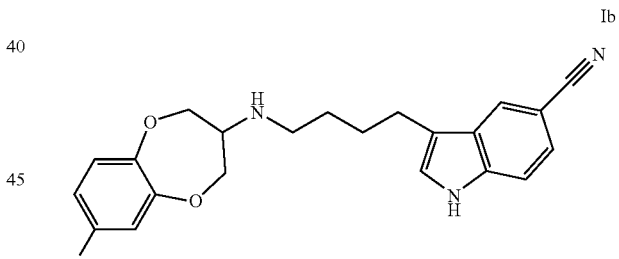

3-{4-[7-Methyl-3,4-dihydro-2H-1,5-benzodioxepin-3-ylamino]butyl}indole-5-carbonitrile Ic

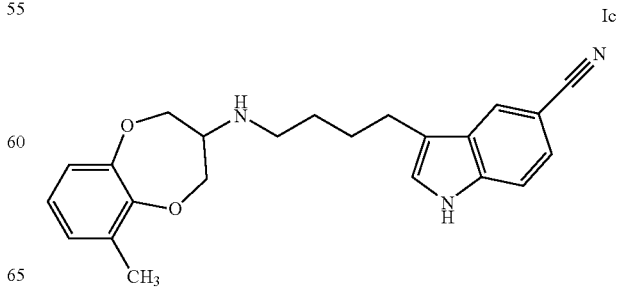

3-{4-(6-Methyl-3,4-dihydro-2H-1,5-benzodioxepin-3-ylamino)butyl}indole-5-carbonitrile

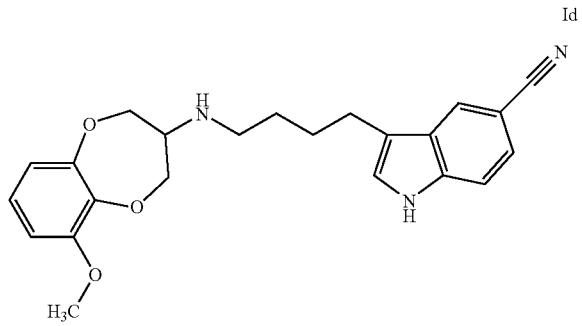

Id

3-[4-(6-Methoxy-3,4-dihydro-2H-1,5-benzodioxepin-3-ylamino)butyl]indole-5-carbonitrile

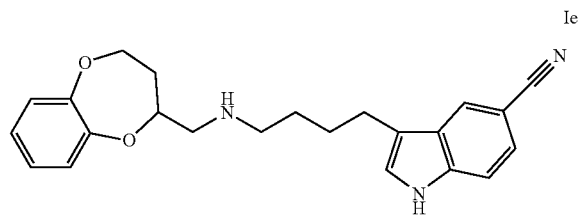

Ie

3-[4-(3,4-Dihydro-2H-1,5-benzodioxepin-3-yl)methylamino)butyl]indole-5-carbonitrile The compounds of the formula I according to the invention may, independently of the choice of the substituents and radicals described above, have one or more chiral centres, in particular one or more chiral carbon atoms. If a compound of defined composition according to the invention has one or more chiral centres, this compound of defined composition may be in the form of different stereoisomers. The present invention relates to all possible such stereoisomers of compounds according to the invention, which may be in the form either of individual, stereochemically uniform compounds, or in the form of mixtures of two or more stereochemically uniform compounds. In the case of mixtures of two or more stereoisomers, the individual stereoisomers may be present in different or identical proportions. In the case of mixtures of two stereoisomers which are present in equal proportions and represent optical antipodes, the term racemic mixtures is used. The present invention likewise relates to racemic mixtures of compounds of the formula I.

The compounds according to the invention can be used as therapeutic agents, diagnostic agents and/or cosmetics or together with one or more active ingredients which are different from the compounds according to the invention and/or adjuvants in the therapeutic agents, diagnostic agents and or cosmetics. The compounds according to the invention are usually employed in the form of pharmaceutical, diagnostic and/or cosmetic formulations. Such formulations and processes for their preparation are known to the person skilled in the art.

Examples of such formulations are suspensions, emulsions, solutions, liposomes, salts, pastes, biodegradable polymers, nanoparticles, tablets, coated tablets, dragees, film tablets, capsules, pills, granules, powders, aerosols, drops or sprays comprising at least one compound according to the invention.

The compounds or formulations according to the invention which comprise at least one compound according to the invention can be administered to humans or animals, for example locally or systemically and in particular orally, intravenously, intraperitoneally, subcutaneously, transdermally, nasally, buccally and/or iontophoretically.

The invention furthermore relates to the use of the compounds of the formula I and/or physiologically tolerated salts thereof for the preparation of pharmaceutical compositions, in particular by non-chemical methods. They can be brought into a suitable dosage form here together with at least one solid, liquid and/or semi-liquid excipient or adjuvant and optionally in combination with one or more further active ingredients.

The invention furthermore relates to pharmaceutical compositions comprising an effective amount of at least one of the compounds of the formula I and/or one of its physiologically tolerated salts.

These compositions can be used as medicaments in human or veterinary medicine. Suitable excipients are organic or inorganic substances which are suitable for enteral (for example oral), parenteral, topical administration or for administration in the form of an inhalation spray and do not react with the novel compounds, for example water, vegetable oils, benzyl alcohols, alkylene glycols, polyethylene glycols, glycerol triacetate, gelatine, carbohydrates, such as lactose or starch, magnesium stearate, talc, Vaseline. Suitable for oral administration are, in particular, tablets, pills, dragees, capsules, powders, granules, syrups, juices or drops, suitable for rectal administration are suppositories, suitable for parenteral administration are solutions, preferably oily or aqueous solutions, furthermore suspensions, emulsions or implants, suitable for topical application are ointments, creams or powders. The novel compounds may also be lyophilised and the resultant lyophilisates used, for example, for the preparation of injection preparations. The compositions indicated may be sterilised and/or comprise adjuvants, such as lubricants, preservatives, stabilisers and/or wetting agents, emulsifiers, salts for modifying the osmotic pressure, buffer substances, colorants, flavours and/or a plurality of further active ingredients, for example one or more vitamins.

For administration as inhalation spray, it is possible to use sprays which comprise the active ingredient either dissolved or suspended in a propellant gas or propellant-gas mixture (for example $CO_2$ or chlorofluoro-carbons). The active ingredient is advantageously used here in micronised form, in which case one or more additional physiologically tolerated solvents may be present, for example ethanol. Inhalation solutions can be administered with the aid of conventional inhalers.

The present invention therefore also relates to processes for the preparation of pharmaceutical compositions which are characterised in that a compound of the formula I and/or one of its physiological tolerated salts and/or one of its solvates is brought into a suitable dosage form together with at least one solid, liquid or semi-liquid excipient or adjuvant.

The compounds according to the invention can generally be administered here analogously to other known compounds having a similar action profile, preferably in dosages of between about 0.05 and 500 mg, in particular between 0.5 and 100 mg, per dosage unit. The daily dose is preferably between about 0.01 and 2 mg/kg of body weight. However, the specific dose for each patient depends on a very wide variety of factors, for example on the efficacy of the specific compound employed, on the age, body weight, general state of health, sex, on the diet, on the time and method of administration, on the excretion rate, medicament combination and severity of the particular disease to which the therapy applies.

The efficacy of the compounds according to the invention for the treatment of diseases of the bladder, in particular of irritable bladder, can be determined using conventional methods known from the prior art, for example using the animal models described below, or analogously thereto.

A model for measuring the effect on urine excretion is described in Lipschitz et al., J. Pharmacol. Exp. Ther. 1943; 79: 97-110. The substance to be investigated is administered to rats which had previously been denied food overnight while being given free access to water. Increased urine excretion is provoked by simultaneous intraperitoneal injection of 100 ml/kg of physiological saline solution. Immediately after administration of the substance, the bladder was emptied by gentle massage of the abdomen above the bladder. The rats are subsequently kept in metabolism cages in which the urine is collected over a period of 6 hours. The compounds according to the invention preferably increase urine excretion as a function of dose, with, for example, it being possible to observe the excretion of a greatly increased amount of urine, preferably at least a 2-fold greater amount of urine, at a dose of about 100 mg/kg. The effect on urine excretion in normal rats is tested analogously (i.e. without induction of increased urine excretion, see above). Here too, the compounds according to the invention preferably increase urine excretion as a function of dose, with it being possible in many cases here to observe the excretion of an increased amount of urine, for example a 5-fold greater amount of urine, even at lower doses of the compounds according to the invention, for example at about 30 mg/kg po.

The classical animal model for irritable bladder is described in Ghoniem et al., Neurourol. Urodyn. 1995; 14: 657-65. In female apes, irritable bladder is induced by direct infusion of acetone into the bladder. The animals are kept in metabolism cages designed for continuous monitoring of miction (urination) of the animals. The frequency, emptying volumes and flow rate of the urine are measured continuously via urine flow meters. Comparison of urea absorption before and after acetone infusion shows that urea absorption is drastically increased after acetone infusion and only reaches the pre-acetone infusion base value again after four weeks. Furthermore, considerable changes in bladder physiology are observed in the first week after acetone infusion: the bladder performance, measured in ml/cm, drops by almost 35%. The emptying behaviour also changes considerably, with the frequency of emptying increasing greatly with the picture of frequent dribbling and at the same time with an emptying volume reduced by about 70%. Systematic observation of the behaviour of the animals over four weeks shows reduced frequency of general and in particular social activities as behaviour repertoire, while stereotypical, self-directed behaviour patterns, such as self-grooming, scratching and fondling, increase considerably. These changes in behaviour observed in apes are consistent with the clinical picture of considerable discomfort and pain. On administration the compounds according to the invention in usual dosages and in particular dosages as described above, such as, for example, dosages of 3, 10, and 30 mg/kg, a dose-dependent normalisation of bladder function can preferably be observed.

EXAMPLE 1

Synthesis of N-(3,4-dihydro-2H-1,5-benzodioxepin-3-yl)-4-(5-cyano-3-indole)butylamine (=EMD 76066)

The synthesis of the starting material used here is known from the literature (Sci. Pharm. 201, 69(1), 11-20).

4 g (24 mmol) of benzo[b]-1,4-dioxepin-3-one and 5.2 g (24 mmol) of 3-(4-aminobutyl)-1H-5-indolecarbonitrile are dissolved in 270 ml of methanol and refluxed for 2 h. After the batch has been cooled to 10° C., 1.4 g (36 mmol) of sodium borohydride are added in portions, and, after one hour, the mixture is refluxed for one hour. The batch is evaporated to dryness and taken up in ethyl acetate.

After washing with water and drying using magnesium sulfate, the residue is chromatographed over a silica-gel column using a 7:3 mixture of ethyl acetate and isopropanol, giving 1.86 g (16%) of N-(3,4-dihydro-2H-1,5-benzodioxepin-3-yl)-4-(5-cyano-3-indole)butylamine.

m.p.: 166-168° C.
CHN calculated: C: 65.39 H: 5.70 N: 8.80
CHN found: C: 65.39 H: 5.82 N: 8.77
$[M+H]^+$, (ESI-MS): 362

EXAMPLE 2

Synthesis of 3-[4-(3,4-dihydro-2H-1,5-benzodioxepin-3-yl)methylamino)-butyl]indole-5-carbonitrile (=EMD 87322)

The synthesis of the starting material used here is known from the literature (J. Med. Chem. 1984, 27, 570).

a) At room temperature, 22.5 ml (81 mmol) of RedAl® are added slowly to a suspension of 5.2 g (27 mmol) of 3,4-dihydro-2H-1,5-benzodioxepin-2-yl)methylamide, which results in a temperature increase to 30° C. The resultant solution is left to cool to room temperature over 2 h. 100 ml of water are subsequently added dropwise, and the mixture is extracted three times with 30 ml of ethyl acetate. The combined organic phases are dried using sodium sulfate and evaporated after the salt has been filtered off. The resultant oil (4.3 g; 83%) is so clean that it can be reacted further without further purification.

b) 4.3 g (24 mmol) of 4-(3,4-dihydro-2H-1,5-benzobenzodioxepin-3-yl)-methylamine are dissolved in 100 ml of acetonitrile, and the solution is refluxed for one hour. After cooling, a solution of 5 g of 3-(4-chloro-butyl)indole-5-carbonitrile is added, and the mixture is refluxed for a further 18 h (TLC monitoring). After cooling of the reaction solution, the latter is evaporated to dryness, stirred with 250 ml of water and extracted three times with 50 ml of diethyl ether. After the organic phase has been dried over sodium sulfate, the solvent is removed in a rotary evaporator, and the resultant 9.2 g of crude substance are purified over a silica-gel column. The product fraction was, after evaporation, precipitated from ethyl acetate and pentane, and the resultant crystals were subsequently recrystallised from diisopropyl ether and ethyl acetate, giving 0.3 g (4%) of the product as monohydrate.

m.p.: 78° C.
$[M+H]^+$, (ESI-MS): 376

An analogous procedure to Examples 1 and 2 gives the compounds:

3-{4-[7-methyl-3,4-dihydro-2H-1,5-benzodioxepin-3-ylamino]butyl}indole-5-carbonitrile (EMD 85350): [M+H]⁺, (ESI-MS): 376

3-{4-(6-methyl-3,4-dihydro-2H-1,5-benzodioxepin-3-ylamino)butyl}indole-5-carbonitrile (EMD 87319); [M+H]⁺, (ESI-MS): 376

3-[4-(6-methoxy-3,4-dihydro-2H-1,5-benzodioxepin-3-ylamino)butyl]indole-5-carbonitrile (EMD 87326); [M+H]⁺, (ESI-MS): 392

EXAMPLE 3

The efficacy of the compounds of the formula I is checked by means of the following investigations:

The serotonin reuptake inhibition was investigated with the aid of synaptosomal uptake inhibition by the method of Wong et al. (Neuropsycho-pharmacol. 8 (1993), 23-33).

The binding properties to the 5HT1A receptor was determined with the aid of the 5-HT1A (serotonin) binding test (Matzen et al., J. Med. Chem., 43 (2000), 1149-1157, in particular page 1156 with reference to Eur. J. Pharmacol.: 140 (1987), 143-155).

In order to determine the binding properties to the 5-HT4 receptor, use was made of the test in accordance with Grossman et al. (Grossman et al., Br. J. Pharmacol. 109, (1993), 618-24).

The following values were found here:

| Compound | 5HT1A ($IC_{50}$ in nmol/l) | 5HT4 ($IC_{50}$ in nmol/l) | SSRI ($IC_{50}$ in nmol/l) |
|---|---|---|---|
| EMD 76066 | 0.5 | n.p. | 8.0 |
| EMD 87322 | 4.0 | 8.4 | 0.6 |
| EMD 85350 | 3.0 | n.p. | 4.0 |
| EMD 87319 | 2.0 | n.p. | 3.0 |
| EMD 87326 | 0.6 | n.p. | 1.0 | n.p. = not performed

The examples below relate to pharmaceutical compositions:

EXAMPLE A

Injection Vials

A solution of 100 g of the active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of the active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of the active ingredient of the formula I, 9.38 g of $NaH_2PO_4 \cdot 2\ H_2O$, 28.48 g of $Na_2HPO_4 \cdot 12\ H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of the active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A benzodioxepine compound of formula I

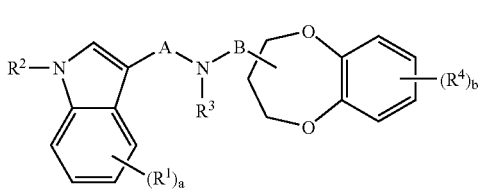

in which
- $R^1$ are, each independently of one another, alkyl, $(CH_2)_m OD$, $(CH_2)_m CN$, $(CH_2)_m COR^5$ or $(CH_2)_m CH_2 R^5$,
- m is 0 or 1,
- $R^2$, $R^3$ are, each independently of one another, H, or alkyl having 1 to 5 C atoms,
- $R^4$ are, each independently of one another, alkyl having 1 to 5 C atoms, heteroalkyl having 1 to 5 C atoms, alkoxy having 1 to 5 C atoms, alkoxyalkyl having 2 to 5 C atoms, Hal, CN, $COR^5$ or OH,
- $R^5$ stands for OD, $NH_2$, NHD or $ND_2$,
- A stands for $C_n H_{2n}$,
- n is 2, 3, or 4,
- B stands for $C_p H_{2p}$,
- p is 0, 1, 2, 3 or 4,
- D are, each independently of one another, H, alkyl having 1 to 5 C atoms, alkoxyalkyl having 2 to 5 C atoms, aryl or aralkyl
- a, b stand for 0, 1 or 2, and
- Hal stands for F, Cl, Br or I, or a pharmaceutically acceptable salt or solvate thereof.

2. A compound according to claim 1, wherein $R^2$ and $R^3$ stand for H.

3. A compound according to claim 1, wherein $R^2$ and $R^3$ stand for H and at least one radical $R^1$ stands for $(CH_2)_m CN$.

4. A compound according to claim 1, wherein a $(CH_2)_m CN$ is in the 5-position of the indole ring.

5. A compound according to claim 1, wherein A stands for $C_n H_{2n}$ where n=4 and B stands for $C_p H_{2p}$ where p=1 or 0.

6. A compound according to claim 1, wherein $R^1$ stands for $(CH_2)_m CN$ in the 5-position of the indole ring and a stands for 1 and m stands for 0, $R^2$ and $R^3$ stand for H, A stands for $C_n H_{2n}$ where n=4 and B stands for $C_p H_{2p}$ where p=1 or 0.

7. A compound according to claim 1, which is
- N-(3,4-dihydro-2H-1,5-benzodioxepin-3-yl)-4-(5-cyano-3-indolyl)butylamine,
- 3-{4-[7-methyl-3,4-dihydro-2H-1,5-benzodioxepin-3-ylamino]butyl}indole-5-carbonitrile,
- 3-{4-(6-methyl-3,4-dihydro-2H-1,5-benzodioxepin-3-ylamino)butyl}indole-5-carbonitrile,
- 3-[4-(6-methoxy-3,4-dihydro-2H-1,5-benzodioxepin-3-ylamino)butyl]indole-5-carbonitrile, or
- 3-[4-(3,4-dihydro-2H-1,5-benzodioxepin-3-yl)methylamino)butyl]indole-5-carbonitrile.

8. A process for preparing a compound according to claim 1, comprising
a) reacting a compound of formula II

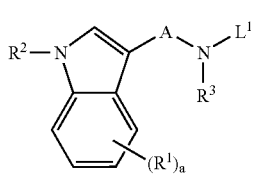

in which $L^1$ denotes H or a metal ion and $R^1$, $R^2$, $R^3$, A and a have the meanings indicated in claim 1, b) with a compound of formula III

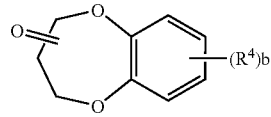

in which $R^4$ and b have the meanings indicated in claim 1,
c) optionally reducing the resultant compound, and
d) optionally converting the resultant compound into one of its salts by treatment with an acid.

9. A process for preparing a compound according to claim 1 or a pharmaceutically acceptable salt or solvate thereof, comprising
a) reacting a compound of formula IV

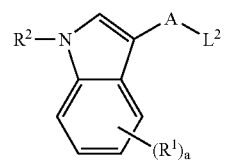

in which $L^2$ denotes Cl, Br, I, OH, a reactively esterified OH group or a diazonium group and $R^1$, $R^2$, A and a have the meanings indicated in claim 1,
b) with a compound of formula V

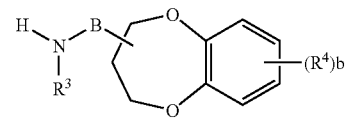

in which $R^3$, $R^4$, B and b have the meanings indicated in claim 1, and optionally
c) converting the resultant compound of formula I into one of its salts by treatment with an acid.

10. A process for preparing a pharmaceutical composition, comprising binging into a dosage form at least one compound of formula I according to claim 1 or a pharmaceutically acceptable salt or solvate thereof with at least one pharmaceutically acceptable solid, liquid or semi-solid excipient or adjuvant.

11. A pharmaceutical composition, comprising a compound of formula I according to claim 1 or a pharmaceutically acceptable salt or solvate thereof, and a pharmaceutically acceptable excipient or adjuvant.

12. A compound according to claim 4, wherein a stands for 1.

13. A compound according to claim 4, wherein m stands for 0.

14. A compound according to claim 1, which is said compound or a pharmaceutically acceptable salt of said compound.

15. A compound according to claim 1, which is
- N-(3,4-dihydro-2H-1,5-benzodioxepin-3-yl)-4-(5-cyano-3-indolyl)butylamine,
- 3-{4-[7-methyl-3,4-dihydro-2H-1,5-benzodioxepin-3-ylamino]butyl}indole-5-carbonitrile, 3-{4-(6-methyl-3,4-dihydro-2H-1,5-benzodioxepin-3-ylamino)butyl}indole-5-carbonitrile, 3-[4-(6-methoxy-3,4-dihydro-2H-1,5-benzodioxepin-3-ylamino)butyl]indole-5-carbonitrile, or 3-[4-(3,4-dihydro-2H-1,5-benzodioxepin-3-yl)methylamino)butyl]indole-5-carbonitrile, or a pharmaceutically acceptable salt thereof.

16. A compound according to claim 1, wherein $R^2$ and $R^3$ stand for H, or a pharmaceutically acceptable salt thereof.

17. A compound according to claim 1, wherein $R^2$ and $R^3$ stand for H and at least one radical $R^1$ stands for $(CH_2)_mCN$, or a pharmaceutically acceptable salt thereof.

18. A compound according to claim 1, wherein a $(CH_2)_m CN$ is in the 5-position of the indole ring, or a pharmaceutically acceptable salt thereof.

19. A compound according to claim 1, wherein A stands for $C_nH_{2n}$ where n=4 and B stands for $C_pH_{2p}$ where p=1 or 0, or a pharmaceutically acceptable salt thereof.

20. A compound according to claim 1, wherein $R^1$ stands for $(CH_2)_mCN$ in the 5-position of the indole ring and a stands for 1 and m stands for 0, $R^2$ and $R^3$ stand for H, A stands for $C_nH_{2n}$ where n=4 and B stands for $C_pH_{2p}$ where p=1 or 0, or a pharmaceutically acceptable salt thereof.

* * * * *